(12) United States Patent
Urey et al.

(10) Patent No.: US 10,054,565 B2
(45) Date of Patent: *Aug. 21, 2018

(54) METHOD AND AN APPARATUS FOR THE DETECTION OF A TAGGING MATERIAL IN FLUIDS

(71) Applicants: KOC UNIVERSITESI, Istanbul (TR); KUANTAG NANOTEKNOLOJILER GELISTIRME VE URETIM A.S., Istanbul (TR)

(72) Inventors: Hakan Urey, Istanbul (TR); Havva Yagci Acar, Istanbul (TR); Caglar Elbuken, Ankara (TR); Basarbatu Can, Istanbul (TR); Osman Vedat Akgun, Izmir (TR); Fahri Kerem Uygurmen, Istanbul (TR)

(73) Assignees: Koc Universitesi, Istanbul (TR); Kuantag Nanoteknolojiler Gelistirme ve Uretim A.S., Istanbul (TR)

(*) Notice: Subject to any disclaimer, the term of this patent is extended or adjusted under 35 U.S.C. 154(b) by 0 days.

This patent is subject to a terminal disclaimer.

(21) Appl. No.: 15/785,441

(22) Filed: Oct. 17, 2017

(65) Prior Publication Data
US 2018/0038826 A1 Feb. 8, 2018

Related U.S. Application Data

(63) Continuation of application No. 14/437,178, filed as application No. PCT/EP2012/070947 on Oct. 23, 2012, now Pat. No. 9,791,407.

(51) Int. Cl.
*G01N 27/447* (2006.01)
*G01N 33/28* (2006.01)
(Continued)

(52) U.S. Cl.
CPC ............ *G01N 27/447* (2013.01); *C10L 1/003* (2013.01); *G01N 21/643* (2013.01); *G01N 21/6428* (2013.01); *G01N 33/2882* (2013.01)

(58) Field of Classification Search
CPC ............. G01N 21/643; G01N 21/6428; G01N 27/221; G01N 27/447; G01N 33/2882;
(Continued)

(56) References Cited

U.S. PATENT DOCUMENTS

| 4,649,711 A | 3/1987 | Sibley et al. |
| 4,745,285 A | 5/1988 | Recktenwald et al. |

(Continued)

FOREIGN PATENT DOCUMENTS

| AU | 2012100395 A4 | 5/2012 |
| EP | 0257559 A2 | 3/1988 |

(Continued)

OTHER PUBLICATIONS

Hu, S.; Gao, X., Stable Encapsulation of Quantum Dot Barcodes with Silica Shells, Adv. Funct. Mater., 2010, 20, 3721-3726.

*Primary Examiner* — Gurpreet Kaur
(74) *Attorney, Agent, or Firm* — Halit N. Yakupoglu (57) ABSTRACT

The present invention relates to a real time identification method of working/functional fluid products including a specified tagging material and an apparatus which is first capturing and then identifying the tagging material using a concentrator and an optical detector, simultaneously transferring the reading to a smart unit and finally releasing the tagging material.

20 Claims, 7 Drawing Sheets

(51) Int. Cl.
*G01N 21/64* (2006.01)
*C10L 1/00* (2006.01)

(58) Field of Classification Search
CPC .... C10L 1/003; C10L 1/00; B01L 2400/0421; B01L 2400/0424; B03C 5/00; B01D 57/02
See application file for complete search history.

(56) References Cited

U.S. PATENT DOCUMENTS

| | | | |
|---|---|---|---|
| 5,229,298 | A | 7/1993 | Zoumalan |
| 5,279,967 | A | 1/1994 | Bode |
| 5,358,873 | A | 10/1994 | Nowak |
| 5,359,522 | A | 10/1994 | Ryan |
| 5,420,797 | A | 5/1995 | Burns |
| 5,525,516 | A | 6/1996 | Krutak et al. |
| 5,652,810 | A | 7/1997 | Tipton et al. |
| 5,710,046 | A | 1/1998 | Rutledge et al. |
| 5,723,338 | A | 3/1998 | Rutledge et al. |
| 5,742,064 | A | 4/1998 | Infante |
| 5,878,178 | A | 3/1999 | Wach |
| 5,878,772 | A | 3/1999 | Belyea |
| 5,928,954 | A | 7/1999 | Rutledge et al. |
| 5,958,780 | A | 9/1999 | Asher et al. |
| 6,274,381 | B1 | 8/2001 | Pauls et al. |
| 6,312,958 | B1 | 11/2001 | Meyer et al. |
| 6,576,155 | B1 | 6/2003 | Barbera-Guillem |
| 6,598,792 | B1 | 7/2003 | Michot et al. |
| 6,691,557 | B1 | 2/2004 | Rice |
| 6,692,031 | B2 | 2/2004 | McGrew |
| 6,881,381 | B1 | 4/2005 | Asher et al. |
| 7,466,400 | B2 | 12/2008 | Luther et al. |
| 7,763,469 | B2 | 7/2010 | Babichenko et al. |
| 8,158,432 | B2 | 4/2012 | Grof et al. |
| 8,384,891 | B2 | 2/2013 | Carr et al. |
| 8,574,323 | B2 | 11/2013 | Green et al. |
| 8,592,213 | B2 | 11/2013 | Wilkinson et al. |
| 8,744,723 | B2 | 6/2014 | Jones |
| 8,805,592 | B1 | 8/2014 | Booth et al. |
| 2002/0164271 | A1 | 11/2002 | Ho |
| 2004/0248307 | A1 | 12/2004 | Grof et al. |
| 2004/0262400 | A1 | 12/2004 | Chang et al. |
| 2005/0165554 | A1 | 7/2005 | Betancourt et al. |
| 2005/0241989 | A1 | 11/2005 | Sant et al. |
| 2005/0260764 | A1 | 11/2005 | Grigsby et al. |
| 2006/0118741 | A1 | 6/2006 | Ross et al. |
| 2006/0173362 | A1 | 8/2006 | Toms et al. |
| 2007/0064323 | A1 | 3/2007 | Luther et al. |
| 2007/0088600 | A1 | 4/2007 | Lichtinger et al. |
| 2007/0178596 | A1 | 8/2007 | Babichenko et al. |
| 2008/0002927 | A1 | 1/2008 | Furnish |
| 2008/0021983 | A1 | 1/2008 | Dodson |
| 2008/0215719 | A1 | 9/2008 | Swan |
| 2009/0289113 | A1 | 11/2009 | Vilnai et al. |
| 2009/0307032 | A1 | 12/2009 | Tribe et al. |
| 2009/0322544 | A1 | 12/2009 | McDowell |
| 2010/0089486 | A1 | 4/2010 | Koeninger et al. |
| 2010/0208243 | A1 | 8/2010 | Suzuki et al. |
| 2010/0222917 | A1 | 9/2010 | Bohlig et al. |
| 2010/0305885 | A1 | 12/2010 | Ganapathy et al. |
| 2011/0040503 | A1 | 2/2011 | Rogers et al. |
| 2011/0101094 | A1 | 5/2011 | Call |
| 2011/0120589 | A1 | 5/2011 | Evans |
| 2011/0130882 | A1 | 6/2011 | Perez |
| 2011/0177494 | A1 | 7/2011 | Ismagilov et al. |
| 2011/0229983 | A1 | 9/2011 | Wilkinson et al. |
| 2012/0034702 | A1 | 2/2012 | Croud et al. |
| 2012/0035442 | A1 | 2/2012 | Barman et al. |
| 2012/0054201 | A1 | 3/2012 | Fischer |
| 2012/0104278 | A1 | 5/2012 | Downing et al. |
| 2012/0205449 | A1 | 8/2012 | Lewis et al. |
| 2012/0301872 | A1 | 11/2012 | Tormod |
| 2013/0009119 | A1 | 1/2013 | Natan et al. |
| 2013/0155402 | A1 | 6/2013 | Walton et al. |
| 2013/0179090 | A1 | 7/2013 | Conroy et al. |
| 2013/0283893 | A1 | 10/2013 | Earl et al. |
| 2014/0236444 | A1 | 8/2014 | Stefan et al. |

FOREIGN PATENT DOCUMENTS

| | | |
|---|---|---|
| EP | 0358203 A1 | 3/1990 |
| EP | 0489347 A1 | 6/1992 |
| EP | 0935750 B1 | 4/2002 |
| EP | 1441227 A2 | 7/2004 |
| EP | 1794764 B1 | 7/2011 |
| FR | 2566909 A1 | 1/1986 |
| GB | 1596521 A | 8/1981 |
| WO | 9412874 A1 | 6/1994 |
| WO | 0177391 A1 | 10/2001 |
| WO | 02098199 A2 | 12/2002 |
| WO | 2006036388 A2 | 4/2006 |
| WO | 2008019448 A1 | 2/2008 |
| WO | 2009026665 A1 | 3/2009 |
| WO | 2009063471 A2 | 5/2009 |
| WO | 2009120563 A1 | 10/2009 |
| WO | 2010089587 A2 | 8/2010 |
| WO | 2011037894 A1 | 3/2011 |
| WO | 2011123938 A1 | 10/2011 |
| WO | 2011132079 A1 | 10/2011 |
| WO | 2013079974 A1 | 6/2013 |
| WO | 2013126028 A2 | 8/2013 |
| WO | 2014087359 A1 | 6/2014 |

METHOD AND AN APPARATUS FOR THE DETECTION OF A TAGGING MATERIAL IN FLUIDS

CROSS-REFERENCE TO RELATED APPLICATIONS

This application is a continuation of U.S. patent application Ser. No. 14/437,178 filed Apr. 20, 2015, which is the U.S. National Stage of International Application No. PCT/EP2012/070947, filed Oct. 23 2012; each of these applications is specifically incorporated herein by reference in its entirety

FIELD OF THE INVENTION

Present invention relates to a real time (online) identification method of working/functional fluid products comprising a specified tagging material and an apparatus which is first capturing and then identifying the tagging material by using concentrator and optical detector, simultaneously transferring the reading to the smart unit and finally releasing the tagging material.

BACKGROUND

Since product counterfeiting, product adulteration, unauthorized distribution and sale of products as well as false liability based on product substitution are major problems for manufacturers, it is important to identify the origin or the grade quality of fluid products like working/functional fluids during storage, transportation, distribution and in use.

Working/functional fluids comprise engine oils, petroleum products, aqueous urea solutions (like AUS32), heat transfer fluids, transmission and hydraulic fluids, metalworking fluids, dielectric fluids.

Branded products i.e. lubricating oils or petroleum fuels can be tampered by dilution with lower or unspecified grade products. Consumers who are willing to pay more money for their expensive equipment or machine may lose their belief for the reputation of branded products, if product they buy has been counterfeited or adulterated. These adulterations result in lower performance of the equipment/machine in which these working/functional fluids are used.

There is also a need, for example, in case of an accident to identify the origin of the leaking or spilling fluid products from an unknown source to understand and evaluate their environmental risks. Furthermore, the source of the spill or leak may be identified and responsible parties should be fined for the act.

It is known that there is a strong request from the manufacturers to use tagging material for identification of the various fluid products for example, petroleum based hydrocarbon products. Tagging may help to trace the identity of fluids, and to identify various grades, and to distinguish manufacturer's brand in order to prevent any product adulteration.

It is common to use tagging materials or markers for variety of fluid products for example petrol based hydrocarbon products, in the form of dyes or colorants. Since these products have high absorption and/or fluorescence in the region of spectrum below 600 nm, it may be preferred to use tagging material or marker absorbing and/or fluorescing above 600 nm.

U.S. Pat. No. 5,928,954 discloses a method for tagging petroleum based hydrocarbon products, such as gasoline, diesel, heating oil, lubricating oil or crude petroleum. A small amount of a fluorescent dye (0.01-1000 ppm by weight) is blended as a marker with petroleum based hydrocarbon products. The presence of the marker in the products is subsequently determined by the excitation of the fluorescent dye and detection of its emission at a dye-specific wavelength, preferably between 630-830 nm. Each and every dye needed to be excited at a different wavelength.

U.S. Pat. No. 5,525,516 describes a method for imparting invisible markers to petroleum based hydrocarbon products for identification purposes. The near infrared emitting fluorophores at low levels are added to petroleum based hydrocarbon products as markers and detected by exposing the marked product compositions to near infrared radiation having a wavelength in the 670-850 nm range and then detecting the emitted fluorescent light via near infrared light detection means.

U.S. Pat. No. 6,274,381 discloses a method for the identification of petroleum based hydrocarbon products tagged with one or more visible dyes with absorption maximum between 500-700 nm at a level less than 1 ppm and detecting the presence of the dyes upon exposing them to radiation between these wavelengths and recording the absorption of dyes and quantifying their concentration based on absorption amounts with a detection equipment sensitive in this spectral region.

WO 2009 120563 A1 describes a method using a marker in a functional fluid, employed in the variety of automotive, off-highway vehicles, on-highway vehicles, equipment, machines, metal working and industrial applications, which survives during the use of the functional fluid in an application with a reagent solution to identify the functional fluid rapidly either before, during or after the functional fluid's use and which is a suitable method for the identification of a functional fluid in the field. A sample of the marked functional fluid before, during or after the fluid's use is obtained, said sample and a reagent solution are placed on a test medium such that they are in contact with each other and the marker in the functional fluid sample is reacted with the reagent solution on the test medium to produce a visible change. Then the resultant visible change is determined and compared with the original functional fluid. Selected marker substances can be one of diazo dyes, anthraquinone dyes, phthalein dyes, and the like, metals, metal salts, metal oxides, metal coordination complexes and the like.

Patent application US2005/0260764 A1 relates to methods for the identification or authentication of liquid products e.g. a petroleum product by the addition of an anti-Stokes marker. The method includes adding an anti-Stokes luminescent marker compound to the liquid followed by exposing the compound to a light source of a known wavelength or known wavelengths and then detecting one or more shorter wavelength emissions from the marker, where the identity of the liquid is confirmed by the emission wavelength or wavelengths that are detected and quantified.

The detection of dye markers in the above methods requires taking a sample from the petroleum based hydrocarbon products already blended with marker, and followed by analyzing with a suitable laboratory apparatus. Therefore, these methods are so called off-line identification of the marker and generally inconvenient and time consuming. Besides, this approach does not inform the end user at the time of the operation but rather can be used after a complaint.

US2005/0241989 A1 discloses a lubricating oil identification system including a lubricating oil composition containing a passive marker which is detected in situ by a detector installed in an engine. Lubricating oil is filled into the machine comprising a detector and an electronic control unit or machine management chip. Then it is detected whether a passive marker is present in said lubricating oil and the information regarding to the status of the oil passes from the detector to the electronic control unit or machine management chip. The sensor is placed in a machine e.g. the cover of the oil reservoir. Passive markers suitable for the identification system disclosed in US2005/0241989 A1 include microparticles e.g. Radio Frequency Identification (RFID) chips, magnetic tags and biomagnetic tags and molecular species as odourant molecules.

US2007/0064323 A1 discloses a method and a device for the automatic detection of at least one fluorescent and/or light-absorbent indicator contained in a liquid service fluid during the filling of a combustion engine. The detection unit is composed of at least one light source, opto-receiver and measurement section. During the filling of a service fluid into the machine, fluid passes through filler tube which has a measurement section, the light source radiates onto the measurement section when the service fluid flows, and light emanates from the service fluid due to fluorescent effect of an indicator present in it. A measurement signal received form the indicator is evaluated and further utilized to determine automatically the identity of the engine oil. In addition, the number of indicators and their concentrations are considered a multiplicity of encoding options for the engine oils treated with indicator.

Fluorescent organic dyes are popular markers in biotechnology as well. However they have several important limitations. One limitation of organic fluorescent dyes is the absorbance at specific wavelengths. Therefore if a marker is created with a combination of several dyes, excitation at different wavelengths are needed. This limits the number of different dyes that can be used to create different codes since the sensor will require number of different excitation wavelengths which will make the system more complex and increase the cost dramatically. This may not be a dramatic problem in case of an off-line analysis but may be a limiting factor in an on-line analysis. Another limitation of organic dyes is a broad emission profile which causes spectral overlap. This limits the production of large number of optical codes comprised of different dyes. Another limitation of organic dyes is the solubility in hydrocarbon solvents especially for NIR dyes. Photobleaching, luminescence quenching and low extinction coefficient of organic dyes are well known important limitations that impact the analysis time, emission intensity and sensitivity.

Quantum dots (QDOTs) are used in medical and biological applications as markers. Bioconjugates of QDOTs with different active pharmaceutical ingredients have been studied previously. QDOTs are quantum confined semiconductor nanoparticles. QDOTs exhibit luminescence properties when they are excited at a suitable wavelength and exhibit, in part, a size dependent emission wavelength as it is known in the art. QDOTs offer many advantages over traditional organic fluorescent dyes due to their unique properties such as:

1) continuous absorbance and narrow emission band width, which provides minimal spectral overlap of the emission originating from different QDOTs;

2) ability to excite QDOTs emitting at different wavelengths at a single wavelength with a single excitation source, which simplifies the design for the excitation device and reduces the cost;

3) ability to tune emission wavelengths by the size of the semiconductor crystal and/or by the composition of the QDOT in a broad spectral region;

4) large absorbance cross-section and high molar absorptivity of QDOTs which can reduce the detectable level of the emitted light intensity;

5) long luminescent lifetime of QDOTs which allow longer analysis time. QDOTs are investigated as optical codes or tags mainly in the field of biotechnology. First two unique characteristics of QDOTs mentioned above allow the generation of large number of optical codes since the numbers of codes that can be created with fluorescent materials are given as "$n^m-1$" for "m" colors with "n" intensity levels. Also, surface of QDOTs can be functionalized as hydrophilic or hydrophobic to suspend in aqueous or organic (oily) medium. Therefore, QDOTs have a great potential to create a large number of distinct optical codes compared to organic fluorescent dyes and may create signal at much lower doses. Examples include QDOT-doped mesoporous microbeads (S. H. Hu, X. Gao, Advanced Functional Materials, 2010, 20, 3721-3726).

Superparamagnetic nanoparticles are popular class of nanomaterials. These nanoparticles do not possess any net magnetization in the absence of a magnetic field, however they respond strongly to an external magnetic field. If the field is removed, material demagnetizes. Therefore, superparamagnetic nanoparticles, as an example, superparamagnetic iron oxide, known in the art as SPION, is widely used in various fields such as contrast enhancement in MRI, drug delivery, magnetofection, therapy, etc. Magnetic nanoparticles can be dragged to the site of interest with an external magnetic field. This is utilized in many applications such as magnetic drug targeting and magnetofection. Magnetic particles can be captured within a magnetic field and therefore utilized widely in magnetic separation of an analyte, cell, etc. and there are several commercial products and devices for biotechnology utilizing such property.

Microbeads comprised of superparamagnetic nanoparticles and QDOTs are used in the art. European Patent document no. 1 794 764 relates to a method in which magnetic nanoparticles and QDOTs encapsulated in a silica bead and the composition therein. High performance equipment and machine require high performance fuels, lubricants, coolants and other fluid products to obtain full performance as described and proven by the Original Equipment Manufacturers (OEMs). Fluid products tested during the development process of the equipment/machine for their best performance become integral part of them. In order to guarantee high performance of the equipment/machine during their lifetime and to avoid any issue regarding warranty agreements, it is highly important to utilize working/functional fluids standardized by OEM's.

Each solid component of the equipment/machine has an identification number written on them. If a component fails, this number helps to identify the manufacturer and history of the component with a high accuracy. Even though fluid products are integral part of the equipment/machine, they do not have any identification number. OEMs only release specification to define the fluid products for the equipment or machine and recommend the use of specific working/functional fluids. If there is any issue raised (performance loss, failure, worsening of emissions, warranty etc.) concerning these fluids, there is no reliable technique to trace back the manufacturer and history of the fluid that has been used in the equipment/machine. Therefore, there is an urgent need to give an identification number in the form of tagging material to such working/functional fluids and use a method to determine their identities.

U.S. Pat. No. 6,691,557 B1 discloses a method for analyzing the maintenance status of liquid-filled electric equipment comprising a particle analysis of suspended particles and sediment contained in the liquid.

U.S. Pat. No. 4,649,711 A discloses an apparatus and method for infrared qualitative analysis of a fluid independent of the temperature of the fluid. A first signal is generated in response to detected infrared energy passing through the fluid, and a second datum signal is provided for comparison with the first signal.

SUMMARY OF THE INVENTION

The present invention relates to a real time identification method of working/functional fluid products comprising a specified tagging material and an apparatus which is first capturing and then identifying the tagging material by using concentrator and optical detector, simultaneously transferring the reading to the smart unit and finally releasing the tagging material.

The apparatus of the present invention which is adapted to identify the tagged working/functional fluids in real time comprises a main fluid travelling conduit (19) connecting a fluid entry port of the equipment/machine to the apparatus, an attachment section (14) connecting the apparatus to the equipment/machine, an optical measurement section (16), and a smart unit (18) which is adapted to determine the identity of the fluid and further comprising:

a. a splitting region inside said conduit, splitting the conduit into at least two partial conduits: at least one measurement conduit and at least one further alternate conduits for the flow of the working/functional fluid, and a unifying region where the at least one measurement conduit and the at least one further alternate conduits are unified into a main fluid travelling conduit, b. a directing means to direct the tagging material to the measurement conduit by generating electromagnetic force or electrostatic force, c. a tagging material concentrator section located in the vicinity of the measurement conduit comprising magnetic or dielectrophoretic concentrator (10) to employ a magnetic field or an electric field.

The method of the present invention for the real time identification of the working/functional fluid comprises the steps of:

a. adding a tagging material comprising a concentrator material coupled with a light emitting material to the working/functional fluid, b. filling the working/functional fluid by passing through the main fluid travelling conduit from a fluid entry port of the equipment/machine and said main fluid travelling conduit (19) splits into at least two partial conduits: at least one measurement conduit (15) and at least one further alternate conduit for functional fluid flow, c. directing the tagging material to an at least one measurement conduit by a directing means which generates electromagnetic force or electrostatic force, d. capturing the tagging material at tagging material concentrator section comprising magnetic or dielectrophoretic concentrator (10) which employs a magnetic field or an electric field to increase the concentration of the tagging material, e. illuminating the concentrated tagging material with at least one light source to excite the light-emitting material, f. detecting the light emitted from the light-emitting material using at least one photodetector, g. transferring the reading to the smart unit for the determination of the identity of the fluid, and h. releasing the tagging material into the working/functional fluid upon completion of the measurement.

The tagging material in the fluid comprises the concentrator material and the light emitting material. The concentrator material can be a magnetic nanoparticle or a dielectric material. The light emitting material is one or more quantum dots, one or more organic light emitting molecules or a combination thereof. Concentrator material is used to concentrate the tagging material at the site of the tagging material concentrator section. If the concentrator material is magnetic nanoparticle and the light emitting material is quantum dot, magnetic nanoparticle effectively captures QDOT based optical code at the tagging material concentrator section and decrease the necessary level of the tagging material in the fluid that will be marked.

The data e.g. optical code of the tagging material detected by the detector at the optical measurement section and recorded and evaluated by the smart unit communicating with said detector. The smart unit transfers the data to the equipment/machine control unit for further utilization. The smart unit can be a part of the apparatus of the invention or it can be separated from the apparatus.

An object of the invention is to provide a real time identification method for the working/functional fluid products comprising a tagging material.

Another object of the invention is to provide an apparatus, capable of real time identification of working/functional fluids, which is first capturing and then identifying the tagging material by using concentrator and optical detector, simultaneously transferring the reading to the smart unit and finally releasing the tagging material.

Other object of the present invention is to generate number from optically coded tagging material to make use of a registration number for each working/functional fluid as a specific identity.

Further object of the invention is to provide a method which reads out the data from the coded tagging material in the fluid and pass it to the smart unit to compare the identity of the fluid with one already defined and stored for that equipment/machine.

BRIEF DESCRIPTION OF THE DRAWINGS

The features described in the present invention and the corresponding reference numerals are as follows.

| Feature | Numeral |
|---|---|
| Matrix | (1); |
| Tagging material | (2); |
| Concentrator material | (3); |
| Light emitting material | (4); |
| Concentrator | (10); |
| Light source | (11); |

-continued

| | |
|---|---|
| Detector | (12); |
| Filter | (13); |
| Attachment section | (14); |
| Measurement conduit | (15); |
| Optical measurement section | (16); |
| Tagging material concentrator section | (17); |
| Smart Unit | (18); |
| Main fluid travelling conduit | (19); |
| Alternate conduit | (20); |
| Lens | (21); |
| Valve | (22); |
| Splitting region | (23); |
| Unifying region | (24); |
| Directing means | (25); |
| Air gap | (30); and |
| Magnetic flux concentrator | (40). |

DETAILED DESCRIPTION OF THE INVENTION

The present invention relates to a real time (online) identification method of the working/functional fluid products comprising a specified tagging material (2) and an apparatus which is first capturing and then identifying the tagging material (2) by using concentrator (10) and optical detector (12), simultaneously transferring the reading to the smart unit (18) and finally releasing the tagging material (2).

The method comprises identification of the fluid via an apparatus which detects light emitting materials (4) coupled with a concentrator material (3) defined as a tagging material (2). The method of the present invention comprises the steps of:

a. adding a tagging material (2) comprising a concentrator material (3) coupled with a light emitting material (4) to the working/functional fluid, b. filling the working/functional fluid by passing through the main fluid travelling conduit (19) from a fluid entry port of the equipment/machine wherein said main fluid travelling conduit (19) splits into at least two partial conduits: at least one measurement conduit (15) and at least one further alternate conduit (20) for functional fluid flow, c. directing the tagging material to an at least one measurement conduit (15), by a directing means (25) which generates electromagnetic force or electrostatic force, d. capturing the tagging material (2) at tagging material concentrator section (17) comprising magnetic or dielectrophoretic concentrator (10) which employs a magnetic field or an electric field to increase the concentration of the tagging material (2), e. illuminating the concentrated tagging material (2) with at least one light source (11) to excite the light emitting material (4), f. detecting the light emitted from the light emitting material (4) using at least one photodetector (12), g. transferring the reading to the smart unit (18) for the determination of the identity of the fluid, and h. releasing the tagging material (2) into the working/functional fluid upon completion of the measurement.

The working/functional fluids described in the present invention are selected from the group of (but not limited to) engine oils, petroleum products, aqueous urea solutions e.g. AUS32, heat transfer fluids, transmission and hydraulic fluids, metalworking fluids and dielectric fluids.

The tagging material (2) of the present invention comprises a concentrator material (3) and a light emitting material (4). Said tagging materials (2) are added to the working/functional fluids. The concentrator material (3) can be a magnetic nanoparticle or a dielectric material. The light emitting material (4) is one or more quantum dots, one or more organic light emitting molecules or a combination thereof. Light emitting materials used in the tagging material (2) of the invention have specific emission in 380-1100 nm range enabling the detection with Silicon photodetectors (12). Emission in different wavebands can be detected using the appropriate detectors (12). It is also possible to excite the light emitting materials via the absorption of two or more photons using longer wavelength light sources. The excitation wavelengths and the emission wavelengths should be selected to minimize the interference of the absorption and emission wavelengths of the functional fluid, which create a bias signal that can be removed by post-processing of the detected signals.

The apparatus of the present invention is adapted to identify the tagged working/functional fluid products in real time comprising a main fluid travelling conduit connecting a fluid entry port of the equipment/machine to the apparatus, an attachment section connecting the apparatus to the equipment/machine, an optical measurement section, and a smart unit which determines the identity of the fluid and further comprises:

a. a splitting region (23) inside said conduit, splitting the conduit into at least two partial conduits: at least one measurement conduit (15) and at least one further alternate conduit (20) for functional fluid flow, and a unifying region (24) where the at least one measurement conduit (15) and the at least one further alternate conduits (20) are unified into a main fluid travelling conduit (19), b. directing means (25) to direct the tagging material (2) to the measurement conduit by generating electromagnetic force or electrostatic force (15), and c. a tagging material concentrator section (17) located in the vicinity of the measurement conduit (15) comprising magnetic or dielectrophoretic concentrator (10) to employ a magnetic field or an electric field.

The apparatus of the invention is comprised of main fluid travelling conduit (19), attachment section (14), directing means (25), tagging material concentrator section (17), optical measurement section (16) and smart unit (18). The main fluid travelling conduit (19) connects a fluid entry port of the equipment/machine to the apparatus and the splitting region (23) inside said conduit splits the conduit into at least two partial conduits. Said partial conduits are at least one measurement conduit (15) and at least one further alternate conduit (20) for functional fluid flow. There is also a unifying region (24) where the at least one measurement conduit (15) and the at least one further alternate conduits (20) are unified into a main fluid travelling conduit (19). The directing means (25) is used for direct the tagging material (2) to the measurement conduit (15).

The working/functional fluid passes through a main fluid travelling conduit (19) from a fluid entry port of the equipment/machine. There is a concentrator (10) which is magnetic or dielectrophoretic concentrator in the tagging material concentrator section (17). The main fluid travelling conduit (19) is surrounded by the tagging material concentrator section (17). Optical measurement section (16) is located at the tagging material concentrator section (17) and said section comprises at least one light source (11) to excite the light-emitting material and at least one detector (12) e.g. photodetector. Light-source simultaneously excites plurality of light-emitting materials with different spectra. The photodetector (12) has different color filters (13) to identify different emission spectra. Smart unit (18) comprises a data base module, a comparison module, a memory module, a diagnostic module and a transfer module. Detected signal is compared with approved oil library and the results are evaluated and recorded by the smart unit (18). If there is any mismatch based on comparison, a warning message is displayed for the driver/operator.

The apparatus is attached to an equipment/machine utilizing the working/functional fluid by means of the attachment section (14). Preferably, the apparatus is able to be activated when a cap of a part using the fluid comprised by the equipment/machine is opened (for instance an engine oil cap of a vehicle). During the filling of the fluid into the equipment/machine, the fluid passes through the main fluid travelling conduit (19) which is surrounded by the concentrator (10). The concentrator (10) employs a magnetic field or an electric field to capture the tagging material (2) at the tagging material concentration section where the tagging materials (2) are collected. In case magnetic particles are used in the tagging material (2), high magnetic field is generated by the concentrator (10). If dielectric particles are used in the tagging material (2), electric field gradient is generated. Preferably, the electric field is a time-varying field. At the site of detection; the main fluid travelling conduit (19) is modified to ease the capturing of tagging material (2). Concentrated tagging materials (2) are illuminated by a UV source. Emitted light from the light emitting material (4) is collected using photo diodes and then the results are evaluated by the smart unit (18) whether the fluid is verified for the equipment/machine.

Tagging Material

Figure 1:
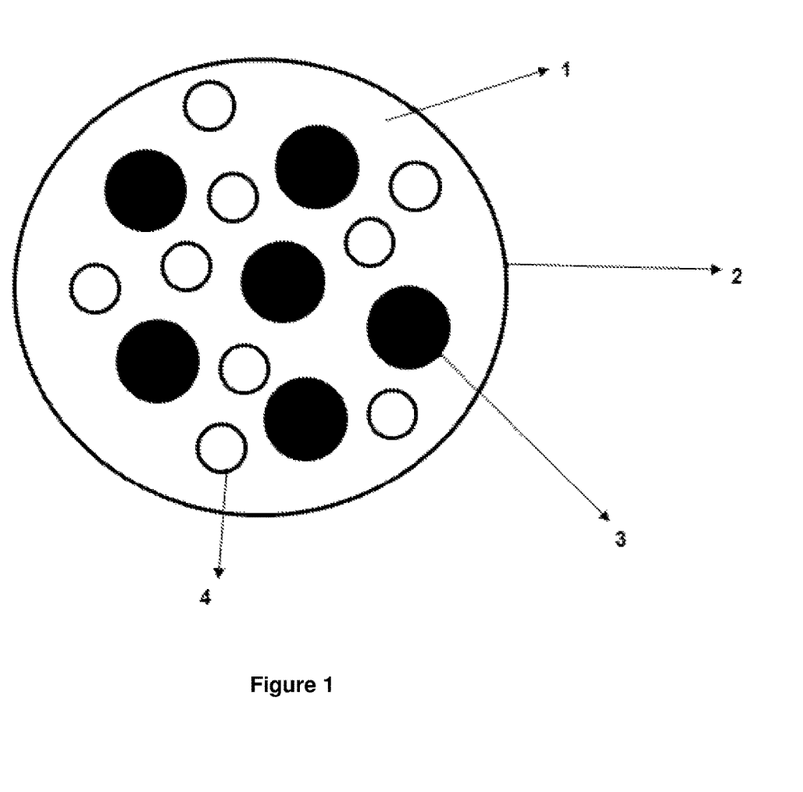
FIG. 1 is a view of the structure of tagging material.

Tagging material (2) of the present invention, which exist in the working/functional fluid, comprise a concentrator material (3) and a light emitting material (4) as shown in FIG. 1. Preferably, the concentrator material (3) is a magnetic nanoparticle or a dielectric material and the light emitting material (4) is one or more QDOTs, one or more organic light emitting molecules or a combination thereof.

In the preferred embodiment, the tagging material (2) is a particle comprising a plurality of magnetic nanoparticles and plurality of semiconductor QDOTs and has a diameter in a range of 10-1000nm. The tagging materials (2) of the present invention are embedded in a capsule or dispersed in a suitable matrix (1).

Tagging materials (2) are used to identify each and every fluid of interest according to the optical signal generated by the tagging material (2). Optical signal is generated by QDOTs and/or organic light emitting molecules upon excitation at a wavelength where they have strong absorbance and by collecting the signal from the emitted photons. Number of tagging materials (2) with different optical codes can be created by both incorporating different types and/or size of QDOTs which emit at different wavelengths and by tuning the ratios of each QDOT in the tagging material (2). Emission wavelength of the light originating from QDOTs and the intensity of the emitted light are used as an optical code specific to each different fluid of interest. The emission spectra and the type of QDOTs or other luminescent molecules used in the tagging material (2) should be tailored depending on the light absorption and emission characteristics of the fluid that will be tagged. Increasing number of different QDOTs incorporated into tagging materials (2) increase the number of possible optical codes that can be created. For the types of fluids, which have strong absorbance in the UV and visible part of the spectrum, QDOTs with strong absorbance at and above 600nm with luminescence in the far-red and NIR region can be preferred. This preference effectively reduces the minimum concentration requirement for detectable optical signal.

Tagging materials (2) comprised of a plurality of QDOTs and magnetic nanoparticles can be formed in the form of a nanosized bead according to the methods known in the art. In accordance with the present invention, the magnetic nanoparticles within the tagging material (2) are utilized to capture and collect the tagging material (2). Magnetic nanoparticles respond to external magnetic field strongly and trapped once the magnetic field is generated by the concentrator (10). Collecting the tagging material (2) aims to increase the concentration of tagging materials (2) required for the detection of the optical code. Once optical reading/recording of the optical code is completed, the magnetic field will be switched off and the tagging material (2) will be released from the tagging material concentration section.

Size of the tagging material (2) is between 10-1000 nm, preferably 200-800 nm and more preferably 200-500 nm. Here, the size is used in terms of a diameter of the tagging material bead considered as a spherical shape. As the magnetic content of the tagging material (2) increases, magnetic capturing ability increases. Therefore, bead size around 200-500 nm is more preferable in functional fluids, especially those used in engine oils, where the particles that are much larger may have adverse effects in the engine performance.

Operation Principle of Apparatus

Figure 2:
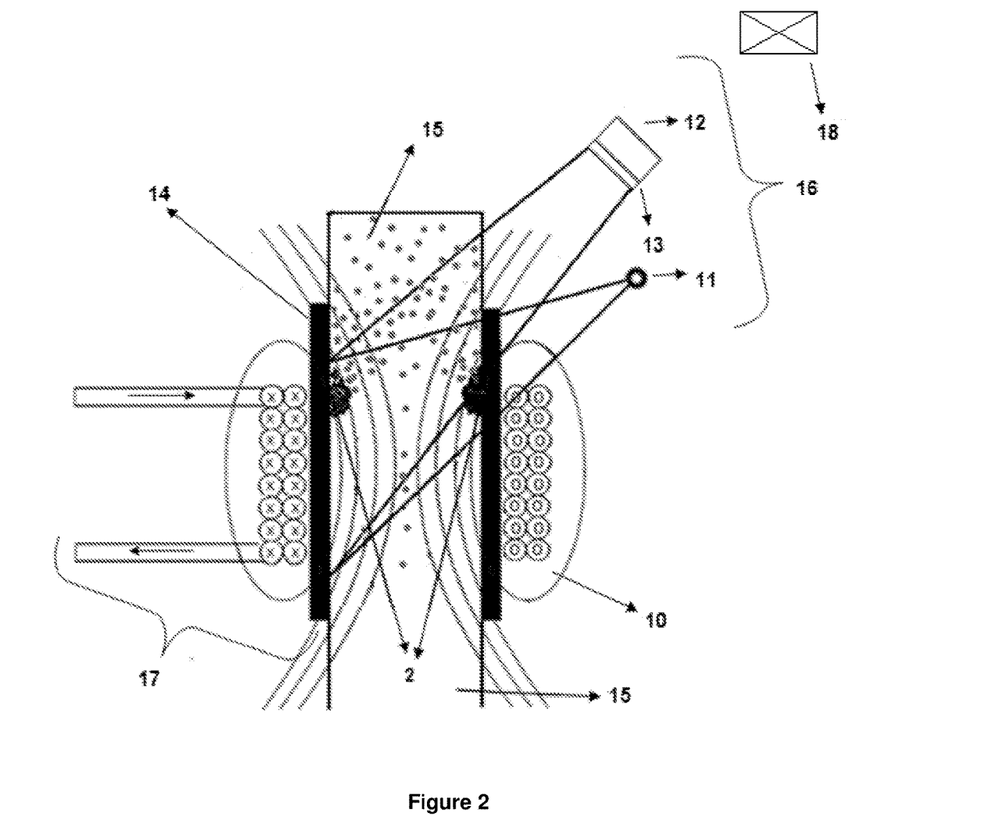
FIG. 2 is a schematic view of an apparatus of the present invention for fluid identification.

Mechanical design of the apparatus of the present invention is shown in FIG. 2. The main fluid travelling conduit (19) is surrounded by a magnetic or an electric concentrator (10), which generates a high magnetic or electrical field gradient. The tagging materials (2) are illustrated as small circles in the fluid. At the tagging material concentration section, the main fluid travelling conduit (19) is modified to slow down the tagging materials. When the concentrator (10) is activated, tagging materials (2) are captured and collected at the regions of high magnetic or electric field gradient. A light-source (11) such as a LED or a laser diode is used to optically excite the light emitting QDOTs and/or organic molecules of the tagging material (2). Plurality of light sources can also be used to create optimal excitation but in the preferred configuration, quantum dots with different emission spectra are excited by a single excitation source. The excited tagging materials (2) emit photons in response to optical absorption. The detector (12) is also demonstrated in FIG. 2. Emitted light can be collected with plurality of photosensitive detectors (12) coupled with optical color filters (13). Transmitted wavelength range of each colour filter (13) is preferable matched to the emission band of the excited tagging materials (2). Detected signal is compared with approved oil library and the results are evaluated and recorded by smart unit (18). If there is any mismatch based on comparison, a warning message is displayed for the driver/operator.

1. Fluid Filling Module

Figure 3:
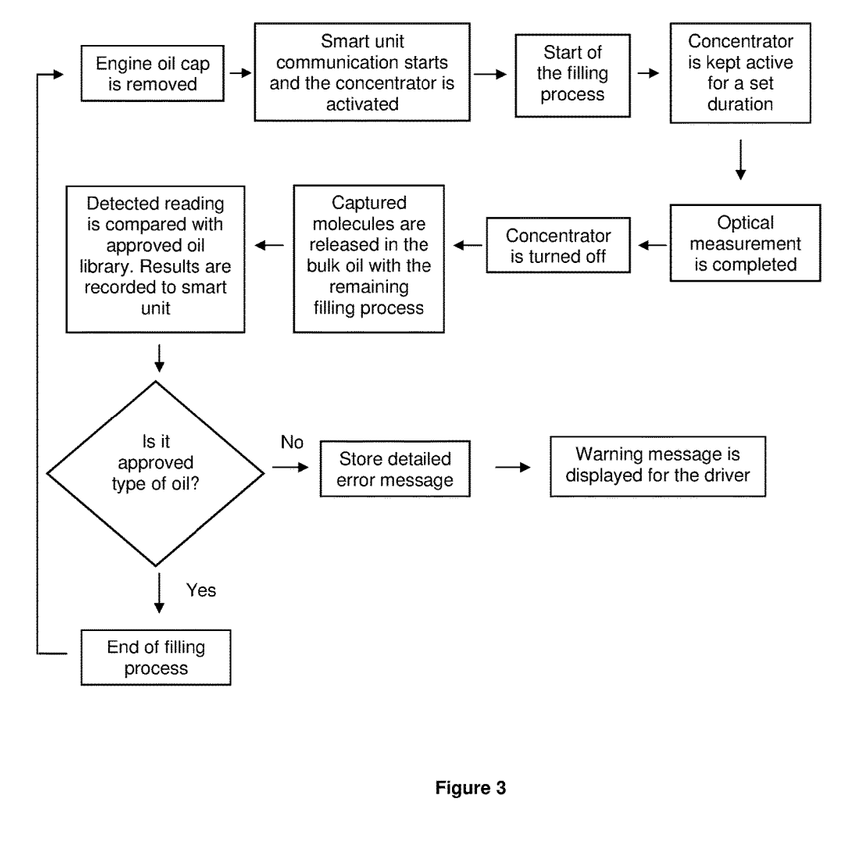
FIG. 3 is a flowchart of the method of the present invention.

The steps of the method of the present invention are summarized in FIG. 3. The apparatus is activated when the fluid entry port of the equipment/machine is opened. For the automobile engine oil application, the apparatus is preferably activated when the engine oil cap is opened. The apparatus which is depicted in FIG. 2 can be designed as a standalone unit, which is separate from the engine, or it can be designed as a part that can be removably or unremovably coupled to the engine oil cap. For a quantitative measurement of the tagging material (2), the volume of the filled fluid should be monitored. This can be achieved by adding a flow sensor to the main fluid travelling conduit 5). In an alternative measurement method, a small volume of fluid is separated in a designated measurement chamber, which allows slowing down the flow of the fluid in the measurement chamber. The volume and the size of this chamber are determined based on the size of the particles and the strength of the optical signal, which is recorded as a function of time.

If the fluid is filled by using a funnel, the measurement is not possible. For the measurement of a fluid in such filling, a folding smart funnel design is considered. The main fluid travelling conduit (19) can be designed to prevent insertion of an unauthorized fluid into the tagging material concentration section. The tagging material concentration section may be placed downstream in the fluid entry port, so that external access to that place is prevented. For ease of operation, a folding funnel design can be considered. The funnel can be designed as a foldable unit and secured next to the engine oil cap when not in use. Before oil replacement operation, the operator can open the funnel by pulling it out of the entrance channel.

Figure 4:
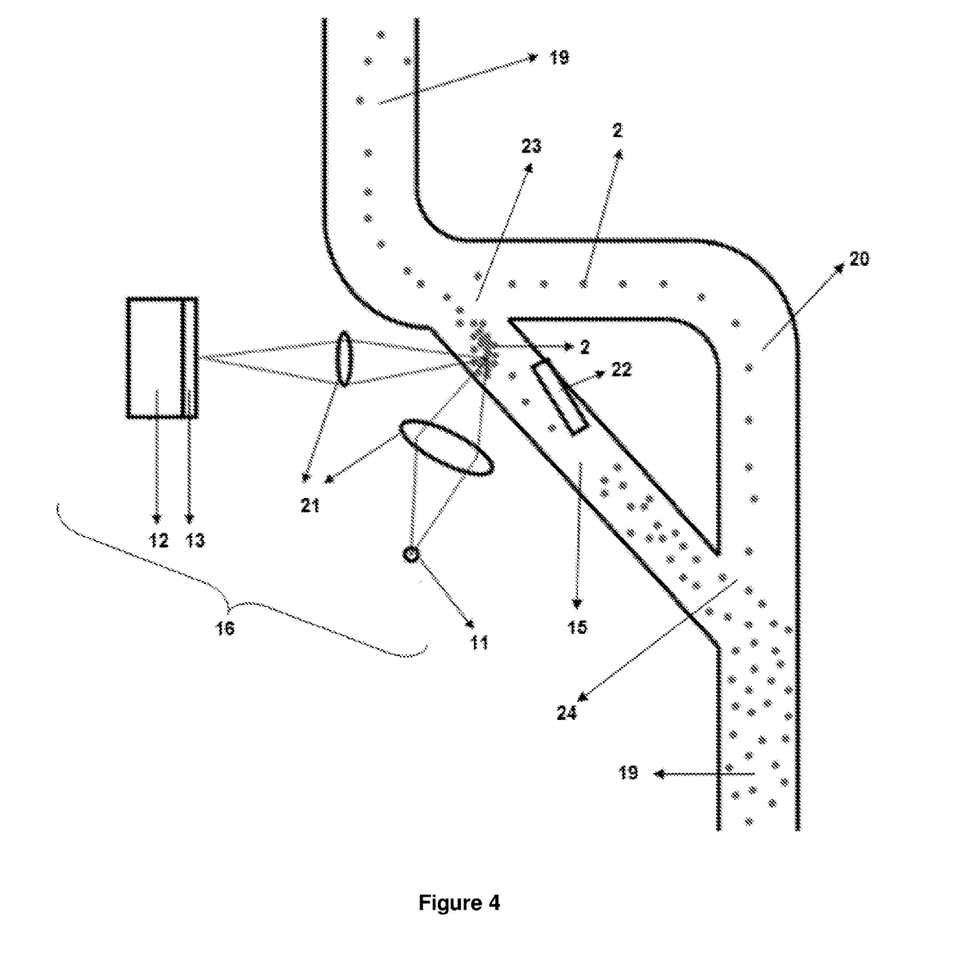
FIG. 4 shows a schematic view of an apparatus of the present invention for fluid identification.
Figure 5:
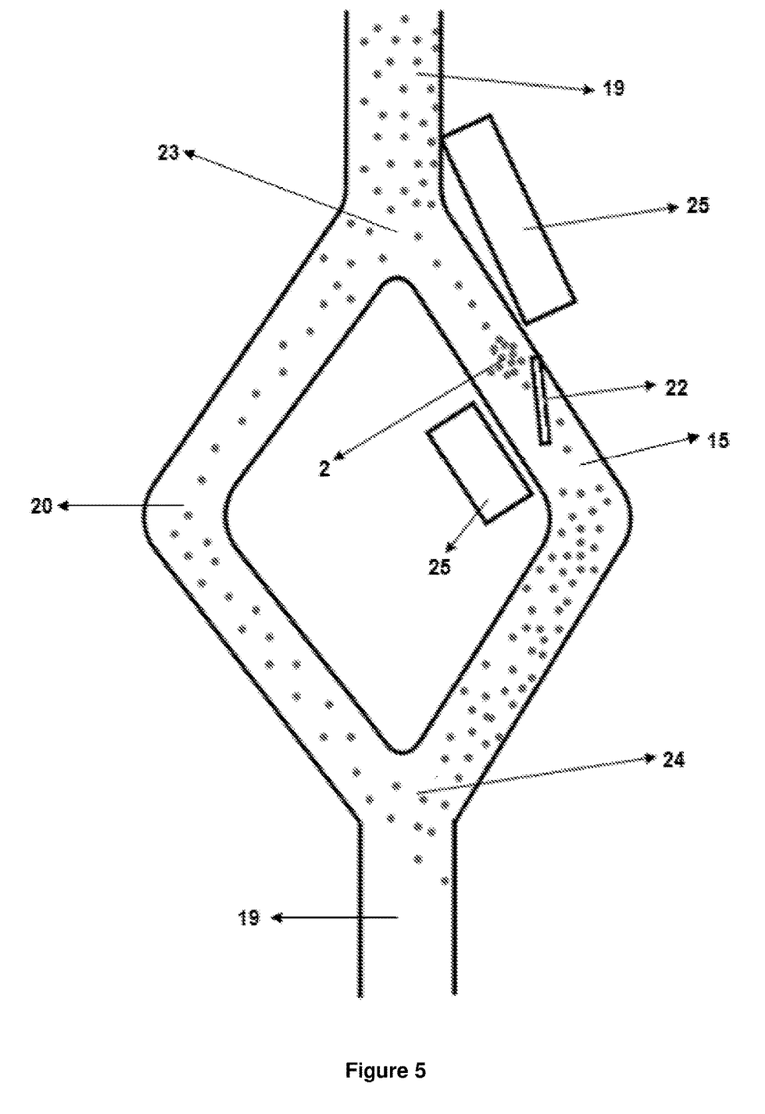
FIG. 5 shows another schematic view of an apparatus of the present invention for fluid identification.
Figure 6:
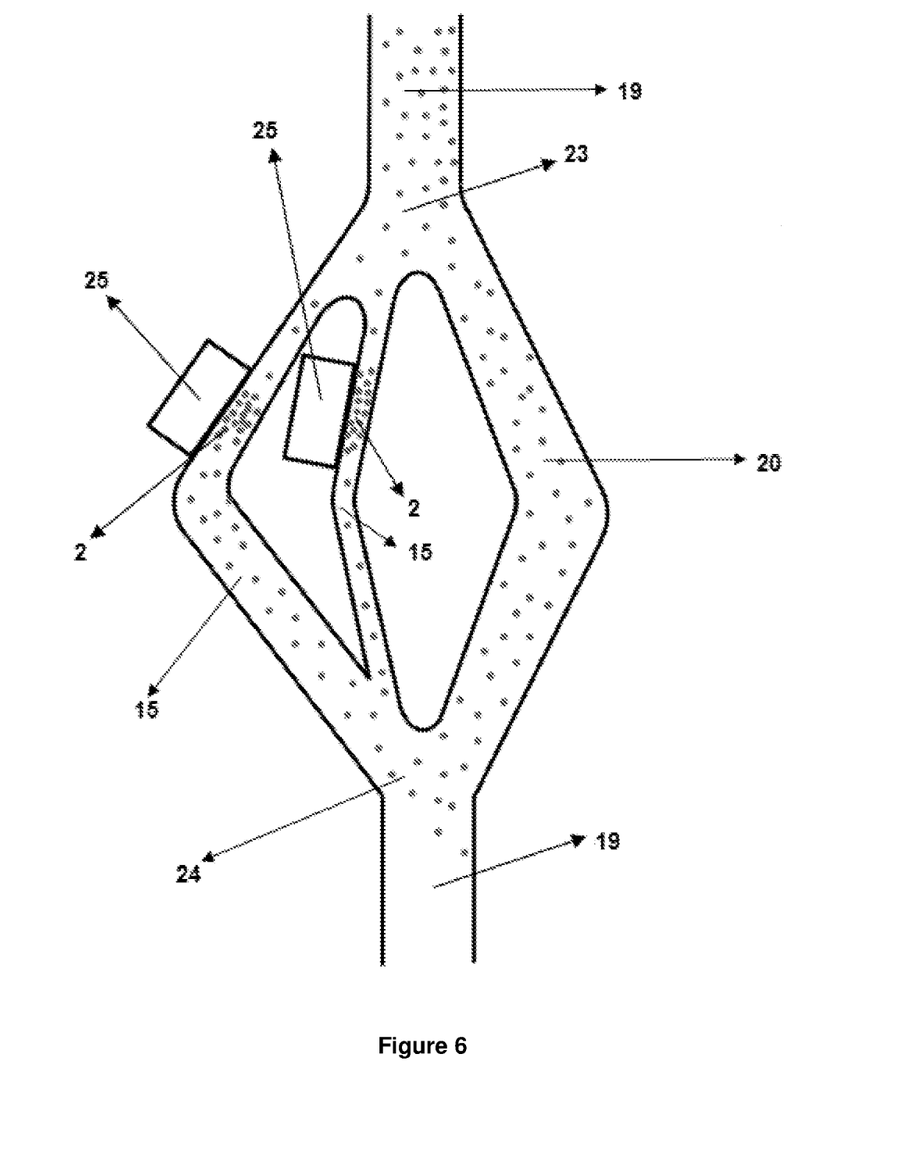
FIG. 6 shows other schematic view of an apparatus of the present invention for fluid identification.

As illustrated in FIG. 4, FIG. 5 and FIG. 6, the device is designed for splitting conduit geometry. Fluid is introduced to the system from the fluid entry port and then travels in the main fluid travelling conduit (19). Main fluid travelling conduit (19) has measurement conduit (15) and at least one or more additional alternate conduit (20). Said measurement conduit comprises tagging material concentrator section (17), optical measurement section, and preferably a smart unit (18). Measurement conduit (15) also comprises a valve (22) for the collection of the marker in that area. Said fluid traveling conduit has a constant or variable cross section. When the fluid is introduced from a fluid entry port of the equipment/machine, the valve (22) is partially closed to slow down the flow of the fluid. Tagging material (2) is directed to the alternate conduit (20) using directing means (25) located the vicinity of the splitting region (23). Directing means (25) is used to direct the tagging particles to the measurement section by generating electromagnetic force or electrostatic force. Said directing means (25) is a magnet, preferably an electromagnet and/or a permanent magnet. The partially closed valve (22) enables the flow of the working/functional fluid while reducing its flow speed and enhancing the capturing of tagging material (2). The flow rate is constant from the fluid filling to the end of the measurement process.

The apparatus of the present invention does not affect the flow rate of the fluid during the introduction of the working/functional liquid into the specific to the equipment/machine. While the fluid flow continues from the main conduit, the magnetic particles are captured in the alternate conduit (20). Preferably, for enhancing the capturing efficacy, the fluid flow rate in the alternate conduit (20) can be slowed down by a modification in the alternate conduit (20).

2. Tagging Material Concentration Section

The main fluid travelling conduit (19) is surrounded by the tagging material concentrator section (17). There is a concentrator (10) in the tagging material concentrator section (17). The concentration of the tagging material (2) in the working/functional fluid should be kept as low as possible not to interfere the characteristics and the function of the working/functional fluid. Detection of very low tagging material concentration can be challenging, therefore a concentrator mechanism is used at optical measurement section.

For concentration of tagging materials (2), two different mechanisms are considered: magnetic concentration and dielectrophoretic concentration.

2.a. Capturing the concentrator particles by magnetic concentrator

In a preferred embodiment, a magnetic concentrator is used to capture the concentrator material (3) in the tagging material (2). Said concentrator material (3) is a magnetic particle.

The tagging materials (2) comprise magnetic particles. The size of this magnetic particle is an important consideration for the design of the system; magnetic nanoparticles are more suitable for this purpose. In order to concentrate the particles using magnetic forces, non-uniform magnetic field is generated across the main fluid travelling conduit (19). The forces acting on a single magnetic particle is shown in equation 1.

$$F_{mag} = \frac{\Delta \chi \cdot V_p}{\mu_0} \cdot (\nabla \cdot B) \cdot B \quad [1]$$

where $\Delta\chi$ is relative susceptibility (susceptibility differences between the magnetic particle and the medium), $V_p$ is the volume of the magnetic particle, $\mu_0$ is the free space permeability, is the magnetic flux density and $\nabla \cdot B$ is the gradient of the magnetic flux density.

When the magnetic particle is moving in a specific direction, drag force acts like friction to decrease the speed of the particle. Drag force ($F_{drag}$) is given in equation 2.

$$F_{drag} = 6 \cdot \pi \cdot r \cdot \eta \cdot u_{flow} \cdot C_w \quad [2]$$

where r is the radius of the tagging material (2), $r_j$ is the viscosity of the medium, $U_{flow}$ is the flow speed of the fluid and $C_W$ is the viscous drag coefficient due to the surface of the top and bottom chamber walls.

Force generated by the magnetic field should dominate the drag force and the resulting speed of the particle should be greater than the flow rate of the fluid for capturing. Net speed of the particle is given in the equation 3.

$$\vec{U}_{res} = \vec{U}_{flow} + \left(\frac{\mu_0 M}{6 \cdot \pi \cdot \eta \cdot r} \cdot \nabla H \cdot \sin\alpha\right) \cdot \vec{e}_x + \left(\frac{\mu_0 M}{6 \cdot \pi \cdot \eta \cdot r} \cdot \nabla H \cdot \cos\alpha\right) \cdot \vec{e}_y \quad [3]$$

where $M$ is the magnetization moment, $\nabla H$ is the gradient of the magnetic field and $\alpha$ is the angle between the force vector acting on the particle and the magnetic flux lines.

Figure 7:
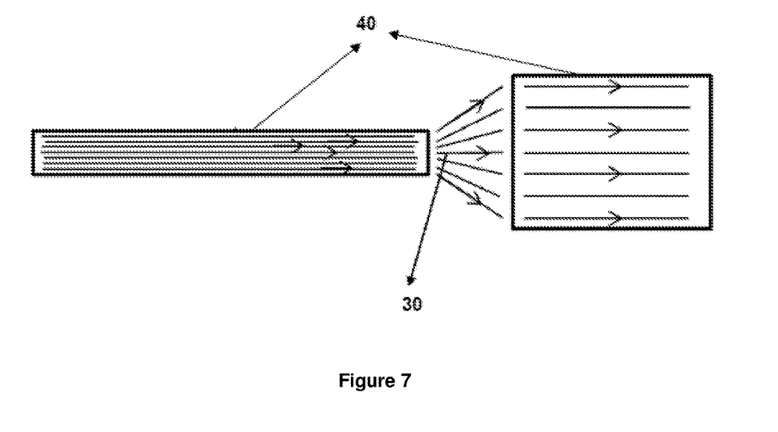
FIG. 7 shows a top view of a magnetic concentrator.

Generating high magnetic field gradient can be achieved by changing the geometry of the magnets as shown in FIG. 7. In this preferred embodiment, two magnetic flux concentrators (40) are separated with an air gap (30). The magnetic flux concentrators (40) are made such that the field lines form a nonuniform magnetic field in the air gap (30). The nonuniform magnetic field generates a magnetic force. The magnets (25) can be permanent magnets or electromagnets. In the permanent magnet case, the amplitude of the magnetic field is controlled by the distance of the magnets which is controlled with the air gap (30) between the magnets. Main fluid travelling conduit (19) is designed to pass through the air gap (30) region. In the electromagnet case, the electrical current controls the magnetic field and its gradient. In both designs, particles are concentrated in the tagging material concentrator section (17) on a small spot where the magnetic field gradient is the highest.

2.b. Capturing the Concentrator Particles by Dielectrophoretic Concentrator

In another preferred embodiment, a dielectrophoretic concentrator can be used instead of the magnetic concentrator.

The tagging material (2) comprises dielectric particles as the concentrator material (3). In order to concentrate particles using dielectrophoretic (DEP) forces, nonuniform electric field is generated across the main fluid travelling conduit (19). Depending on the contrast between the polarizability of particles and the fluid, particles are attracted to local electric field maxima or minima points in the micro channel. The dielectric coefficient of the dielectric particle is different than the fluid medium.

Dielectrophoretic force is generated by placing dielectric particles in a nonuniform electric field. The nonuniform electric field causes the particle to experience an unbalanced electrical attraction force and the particle is attracted towards the direction of increasing or decreasing electric field. This force ($F_{DEP}$) can be calculated using the formulas [4] and [5]:

$$F_{DEP} = 2\pi\varepsilon_0 r^3 \text{Re}[f_{CM}(\omega)]\nabla E_{rms}^2 \quad [4]$$

$$F_{CM(\omega)} = \frac{\varepsilon_p^*(\omega) - \varepsilon_0^*(\omega)}{\varepsilon_p^*(\omega) + 2\varepsilon_0^*(\omega)} \quad [5]$$

where, r is the radius of the dielectric particle, $\varepsilon_o$ is the dielectric constant of fluid, $f_{CM}(\omega)$ is the Clausius-Mossoti factor, $E_{rms}$, is the RMS electric field, $\varepsilon^* = \varepsilon - j\sigma/\omega$ is complex dielectric constant, $\sigma$ is conductivity, $\omega$ is angular frequency, and subscripts p and o refer to the particle and the fluid, respectively.

Figure 8:
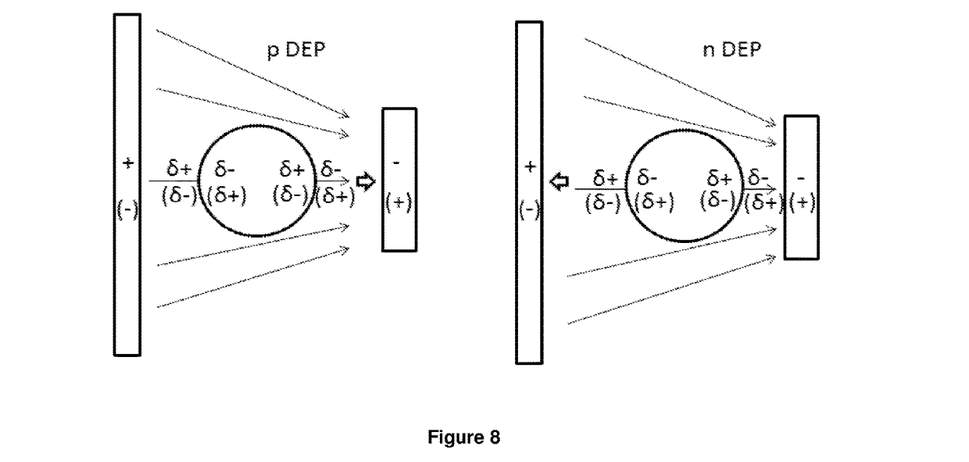
FIG. 8 is a schematic view of the movement of the dielectrophoretic (DEP) particle concentration.

As illustrated in FIG. 8, if the particles are polarized more than the fluid molecules, the generated DEP force will attract the particles in the direction of increasing electric field. This is called positive DEP (pDEP). In case, the working/functional fluid molecules are polarized more than the dielectric particles, the particles will be pushed in the direction of decreasing electric field, which is explained as negative DEP (nDEP).

The separation of particles can be achieved by either using a direct current (DC) electric field or an alternating current (AC) electric field. When DC field is used, the particles experience a Coulomb attraction for based on their net charge. In working/functional fluid, the tagging material (2) may be charged due to extreme working conditions and the content of the working/functional fluid. Therefore, AC electric field is the preferred method to create the DEP force.

In order to generate a non-uniform electric field, uneven electrode geometries is preferably used. The electrode geometry is an exemplary way of generating non-uniform electric field. The geometry of electrodes is determined based on the main fluid travelling conduit (19) and sample collection chamber design. Another way of generating non-uniform electric field is using concentric electrodes where the conduit is located in between. The circular geometry of the electrode will form a nonuniform electric field.

2.c. Enhancement of the Capturing Efficiency

Several design variations such as use of field focusing elements and mesh grid structures can be considered for more effective capturing.

Low-Flow Chamber:

In a preferred embodiment, in order to decrease the flow speed of the working/functional fluid, the geometry of the main fluid travelling conduit (19) can be modified. The concentrator (10) is placed where the flow speed is minimized. At this spot, the collection of the tagging materials is maximized and the optical readout system gives the highest intensity output.

Mesh Filters:

In another preferred embodiment, a sieve like structure is placed on the top of the apparatus in the main fluid travelling conduit (19). The structure is magnetized using magnets. The working/functional fluid flows through the sieve and the collection of the tagging materials (2) are maximized at the bottom of small spot where the field concentrator magnet is placed. This structure provides to get higher output signal from the tagging materials (2) for the optical readout.

Extra Pool:

In another preferred embodiment, an extra pool can be placed in the main fluid travelling conduit (19). Flow speed of the working/functional fluid is minimized in the pool. Field concentrator is placed here and the optical system generates the code signal.

3. Optical Measurement Section

For optical detection of the optical code carried by the tagging material (2), the tagging materials (2) are captured in the tagging material concentrator section (17) and are held at that location during the measurement time. Optical measurement section (16) of the method of the present invention comprises at least one light source (11) and at least one detector (12) e.g. photodetector. Said detector (12) is coupled with optical filters (13) to measure the spectrum of the emitted light and the light source (11) is focused on tagging materials (2) and the emission is collected on the detector (12) using at least one lens (21).

In one embodiment of the invention, collected tagging materials (2) at the tagging material concentration section will be illuminated by a UV source or a visible light source or a near infrared light source. Emitted light from the light emitting material will be collected using photo diodes.

One method to quantify the relative concentrations of different color materials is to use a photodetector array with different color filters (13) such as red, green, blue, and NIR bandpass color filters (13) coupled with a photo detector array. In a preferred implementation, a diffraction grating or a prism structure coupled with a photodetector array can be used to determine the spectrum of the emitted light from the particles.

In FIG. 5, reflected light is collected using a photodetector array, such as a PIN diode array or a quad photo detector that consist of four detectors. Color filters (13) are used to enable computation of concentration of different colored materials in the tagging material (2). Optimal case is to have at least as many detectors as the number of different emission spectra present in the tagging material (2), where the filter (13) for each detector matches the spectral emission response of one of the light emission materials. Additional detectors with narrowband or broadband spectral filters can also be used to increase the signal throughput and to provide reference measurements about the total intensity levels. Number of the emission spectra or colors present in the tagging material (2) and the intensity levels determines the number of the codes that can be generated. Different colors "n" and different intensity "m" levels provide nm unique codes. Upon completion of the optical code reading, the concentrator is turned off and the readings are sent to the smart unit (18) for the further processing. The optical code detected being a registration number for the fluid is compared with approved fluid library stored in the data base and the results are recorded to the smart unit (18). If there is any mismatch based on comparison, a warning message is displayed for the driver/operator. After the measurement is completed, the collected tagging materials (2) are released back to the bulk working/functional fluid by opening the valve (22) in order to allow measurement of next working/functional fluid sample.

4. Smart Unit

Smart unit (18) determines the identity of the working/functional fluid supplied to the equipment/machine and comprises a data base module, a comparison module, memory module, diagnostic module and a transfer module (includes a GPS module). The data base module stores the registration numbers of approved working/functional fluid specific to the equipment/machine. The registration number is coded by a tagging material (2) as a specific identity for each working/functional fluid. The comparison module communicates with the data base module. The comparison module compares the registration number read by the detector of the apparatus with already stored registration number in the data base. The stored data base can be updated via internet or any other means when a new working/functional fluid is registered specific to that equipment/machine. Data base module also can be located at any place other than the equipment/machine to store the data relating to the registration numbers of approved working/functional fluid.

The memory module records all the events based on comparison including mismatch reading by a date, a time of a day, a location, and an amount of working/functional fluid service to the equipment/machine. The diagnostic module receives the data from the memory module and notifies the operator in the form of visual and audio alert. The transfer module sends the data using a communication means to a receiver in the form of electronic mail, SMS or to the WEB site of interested parties. Preferably, smart unit (18) communicates with the equipment/machine electronic control unit (ECU).

We claim:

1. An apparatus for real time identification of tagged working/functional fluids, comprising:
   a main fluid conduit to flow a tagged working/functional fluid including a mixture of tagging materials and a working/functional fluid to be identified, the main fluid conduit connecting a fluid entry port of an equipment/machine to the apparatus;
   a tagging material concentrator section located adjacent the main fluid conduit, the tagging material concentrator section including a magnetic concentrator to apply a magnetic field to capture the tagging materials in the tagging material concentrator section;
   an optical measurement section including at least one light source to illuminate the tagging materials and at least one photodetector to detect emitted light from the tagging materials to determine a unique code which becomes a registration number for the working/functional fluid; and
   a smart unit which is adapted to determine the identity of the working/functional fluid based on the unique code received from the optical measurement section.

2. The apparatus of claim 1, wherein the tagging materials comprise a concentrator material and a light emitting material.

3. The apparatus of claim 1, wherein the main fluid conduit has a constant cross section.

4. The apparatus of claim 1, wherein the main fluid conduit has a variable cross section.

5. The apparatus of claim 1, wherein the flow of the tagged working/functional fluid is adapted to slow down or temporarily stop at the tagging material concentrator section.

6. The apparatus of claim 1, wherein the magnetic concentrator is adapted to capture the tagging materials using magnetic field gradient.

7. The apparatus of claim 6, wherein the magnetic concentrator is a permanent magnet.

8. The apparatus of claim 6, wherein the magnetic concentrator is an electromagnet.

9. The apparatus of claim 6, wherein capturing the tagging materials is enhanced with a low flow chamber in the main fluid conduit.

10. The apparatus of claim 6, wherein capturing the tagging materials is enhanced with a mesh structure placed in the main fluid conduit.

11. The apparatus of claim 6, wherein capturing the tagging materials is enhanced with an extra pool placed in the main fluid conduit.

12. The apparatus of claim 6, wherein captured tagging materials are adapted to be released using a valve on the main fluid conduit upon completion of identification of the tagging materials in the smart unit.

13. The apparatus of claim 1, wherein the at least one photodetector is coupled with optical filters to measure the spectrum of the emitted light which provides the unique code.

14. The apparatus of claim 13, wherein the at least one photodetector has different color filters to identify different emission spectra.

15. The apparatus of claim 13, wherein the emitted light from the tagging materials is adapted to be focused and collected onto the at least one photodetector using at least one lens.

16. The apparatus of claim 1, wherein the working/functional fluid is selected from engine oils, refined petroleum products, aqueous urea solutions, heat transfer fluids, transmission and hydraulic fluids, metalworking fluids and dielectric fluids.

17. The apparatus of claim 2, wherein the concentrator material is a magnetic nanoparticle.

18. The apparatus of claim 2, wherein the light emitting material is at least one of one or more organic light emitting molecules and one or more quantum dots.

19. The apparatus of claim 2, wherein the light emitting material has an emission wavelength between 380-1100 nm.

20. The apparatus of claim 1, wherein the smart unit comprises:
    a database module that stores registration numbers of approved working/functional fluids specific to the equipment/machine;
    a comparison module that compares the registration number read by the at least one photodetector with the registration numbers stored in the database;
    a memory module that records all events based on comparison;
    a diagnostic module that receives data from the memory module; and
    a transfer module that sends the data using a communication means to a receiver.

* * * * *